(12) United States Patent
Zaher et al.

(10) Patent No.: US 7,405,322 B2
(45) Date of Patent: Jul. 29, 2008

(54) MANUFACTURE OF OXALIC ACID DIHYDRATE

(75) Inventors: Joseph J. Zaher, Newark, DE (US); Bryan C. Fritzler, Newark, DE (US); Scott N. Hutchison, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/724,720

(22) Filed: Mar. 16, 2007

(65) Prior Publication Data

US 2007/0197835 A1    Aug. 23, 2007

Related U.S. Application Data

(63) Continuation-in-part of application No. 11/228,378, filed on Sep. 16, 2005, now Pat. No. 7,244,862.

(51) Int. Cl.
*C07C 55/06* (2006.01)
(52) U.S. Cl. .................................................... 562/597
(58) Field of Classification Search ...................... None
See application file for complete search history.

(56) References Cited

U.S. PATENT DOCUMENTS 1,031,074 A * 7/1912 Lidbury ...................... 562/597
7,244,862 B2 * 7/2007 Zaher et al. ................. 562/597

* cited by examiner

*Primary Examiner*—Paul A Zucker

(57) ABSTRACT

A process for the manufacture of oxalic acid dihydrate in which an aqueous solution of sodium oxalate is contacted with hydrochloric acid and the resulting mixture then cooled to precipitate oxalic acid, followed by optional recovery and recycling of the sodium oxalate and hydrochloric acid into the reaction chamber.

27 Claims, 4 Drawing Sheets

US 7,405,322 B2

MANUFACTURE OF OXALIC ACID DIHYDRATE

This application is a continuation-in-part of, and claims the benefit of, U.S. application Ser. No. 11/228,378, filed Sep. 16, 2005, now U.S. Pat. No. 7,244,862, which is incorporated in its entirety as a part hereof for all purposes.

FIELD OF THE INVENTION

The present invention relates to the manufacture of oxalic acid dihydrate.

TECHNICAL BACKGROUND

Oxalic acid (or ethanedioc acid) [HOOCCOOH] dihydrate is currently manufactured by many different routes. One of the most common routes reacts sodium oxalate with lime (calcium oxide) to precipitate calcium oxalate monohydrate and form an aqueous solution of sodium hydroxide. The calcium oxalate monohydrate is separated from the caustic solution and in another reaction step sulfuric acid is used to precipitate calcium sulfate dihydrate and form an aqueous solution of oxalic acid. This aqueous solution of oxalic acid is separated from the calcium sulfate dihydrate and cooled to induce crystallization of oxalic acid dihydrate. The final filtrate is then typically returned to the sulfuric acid addition step since much of the unused sulfuric acid is still contained in this solution. The calcium sulfate dihydrate forms a solid waste byproduct that often requires landfill disposal.

Oxalic acid or its dihydrate is used currently in the following commercial applications: in textile finishing as a bleach or stain remover, as a metal cleaning agent, as wood bleach or wood stain lightener and in the tanning and finishing of leather. It is also used as an additive to increase fertilizers and in artillery ammunition to suppress flashing. These relatively limited commercial uses have not spurred a commercial demand for finding a more efficient method for oxalic acid manufacture; and production by the current manufacture methods has kept pace with the modest worldwide demand for the acid.

Specifically needed to improve the efficiency of oxalic acid dihydrate production is a process made in one reaction chamber, i.e., a one-pot process, and one that is more environmentally benign, such as when the discharge waste salt of such a process is sodium chloride, which need not be disposed in a landfill.

SUMMARY OF THE INVENTION

Disclosed herein is a process comprising:
a) contacting an aqueous solution of hydrochloric acid with sodium oxalate in a reaction zone at a temperature between about 35° C. and about 140° C. to form a mixture, wherein the molar ratio of the water to the sodium oxalate is between 20 to 1 and 350 to 1 and the molar ratio of the hydrochloric acid to the sodium oxalate is greater than 3 to 1 and less than 45 to 1.
b) cooling the mixture to a temperature between about −10° C. and about 25° C. to form precipitated oxalic acid dihydrate in a slurry; and
c) separating the precipitated oxalic acid dihydrate from the slurry, thereby leaving a first residual solution.

Steps a and b may be carried out in one reaction chamber.

The disclosed method may further comprise the steps of recovering both the unreacted hydrochloric acid and the unprecipitated oxalic acid from a residual solution and recycling the recovered hydrochloric acid and the recovered oxalic acid back to the reaction zone. Alternatively, either the unreacted hydrochloric acid or the unprecipitated oxalic acid may be recovered and recycled back to the reaction zone. In any case, the unrecovered oxalic acid may be neutralized with a sodium-containing base solution to form precipitated sodium oxalate, which, after separation from a residual solution, may be recycled back to the reaction zone.

DETAILED DESCRIPTION

Described herein is a process for the manufacture of oxalic acid dihydrate by reacting together hydrochloric acid and sodium oxalate in a certain ratio of molar amounts of these reagents and under certain reaction conditions. This process may be performed in a single reaction chamber as a single reaction step. Both sodium oxalate and hydrochloric acid are inexpensive reagents produced in excess of demand by other industrial processes. Their conversion in a single reaction step into useful oxalic acid dihydrate can reduce the waste streams of other industrial processes. Plus, the waste stream of the currently described oxalic acid dihydrate manufacture is a sodium chloride solution that may be environmentally benign enough for discharge into large bodies of water.

Reacting hydrochloric acid with sodium oxalate may take place in one reaction chamber. Either or both reagents may be recycled back to the beginning or front-end step of the process to further reduce costs and provide an increased amount of starting material. In addition to the novelty of this manufacture, the process of recycling hydrochloric acid and sodium oxalate in this manufacture has not heretofore been practiced.

Definitions

The following definitions explain, illuminate and clarify elements recited in the claims and used herein.

As used herein, "recycling" means sending material from the back end of the manufacture process to the front end.

As used herein, "recovery" is the physical separation of a chemical from a residual solution for the purpose of being recycled.

As used herein, "molar ratio" is the quantitative comparison between the amounts of two chemicals in a mixture, solution, etc., which identifies their stoichiometric relationship to each other and which is typically given as a quotient.

As used herein, "residual solution" is a general term to indicate the solution that remains after the product formed by a separation or a precipitate-forming reaction, has been removed from the reaction mixture.

As used herein, "oxalic acid" refers to oxalic acid in solution and "oxalic acid dihydrate" refers to oxalic acid in crystallized form.

Figure 1:
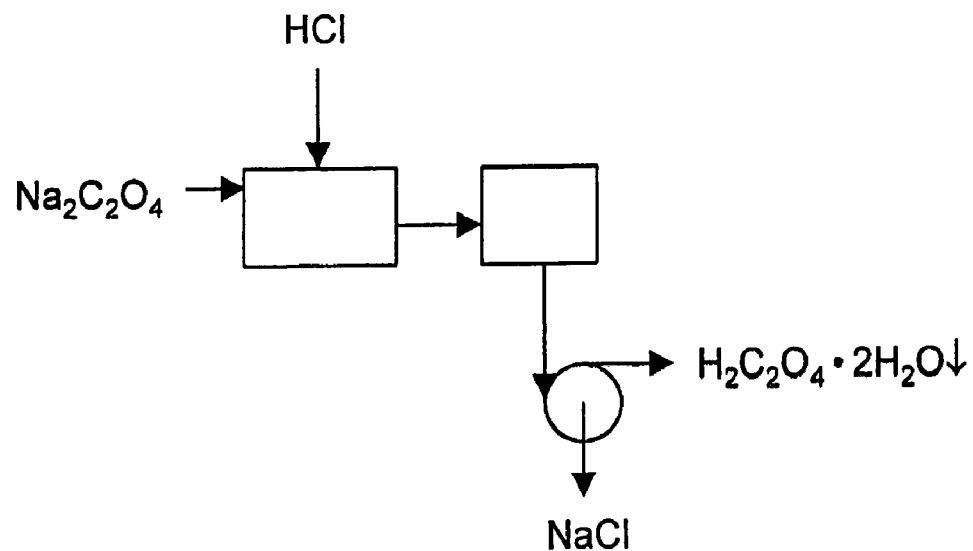
FIG. 1 shows a generalized process of manufacture by reacting sodium oxalate and hydrochloric acid to result in oxalic acid.

FIG. 1 outlines a generalized manufacturing process of oxalic acid. The first step is to contact an aqueous solution of hydrochloric acid with sodium oxalate. The hydrochloric acid used should be in an amount greater than about 2 moles, greater than about 3 moles, greater than about 4 moles, or greater than about 8 moles, but less than about 45 moles per mole of sodium oxalate. The amount of water present should be greater than about 20 moles, or greater than about 35 moles, but less than about 350 moles per mole of sodium oxalate. In alternative embodiments, the concentration of hydrochloric acid in the aqueous solution of hydrochloric acid may be no greater than about 18 wt %, and may alternatively be in the range of about 3 wt % to about 18 wt %. In order to dissolve the sodium oxalate, the reaction should occur at a temperature in the range of about 35° C. to about 140° C. and the reagents should be thoroughly stirred.

The solution of hydrochloric acid and sodium oxalate is then cooled to precipitate solids of $H_2C_2O_4 \cdot 2H_2O$, i.e., oxalic acid dihydrate as indicated by step 2 in FIG. 1. A temperature between about −10° C. and about 25° C. achieves maximum yield. When the hydrochloric acid is present in the amount of 3 moles or less per mole of sodium oxalate, the precipitate formed upon cooling is not oxalic acid dihydrate but crystals of sodium hydrogen oxalate monohydrate.

The third step in FIG. 1 is the separation of the solid oxalic acid dihydrate from the residual solution, which may be accomplished by various techniques well known in the art such as filtration or centrifugation. The solid oxalic acid dihydrate may then be washed, dried and packaged.

Figure 2:
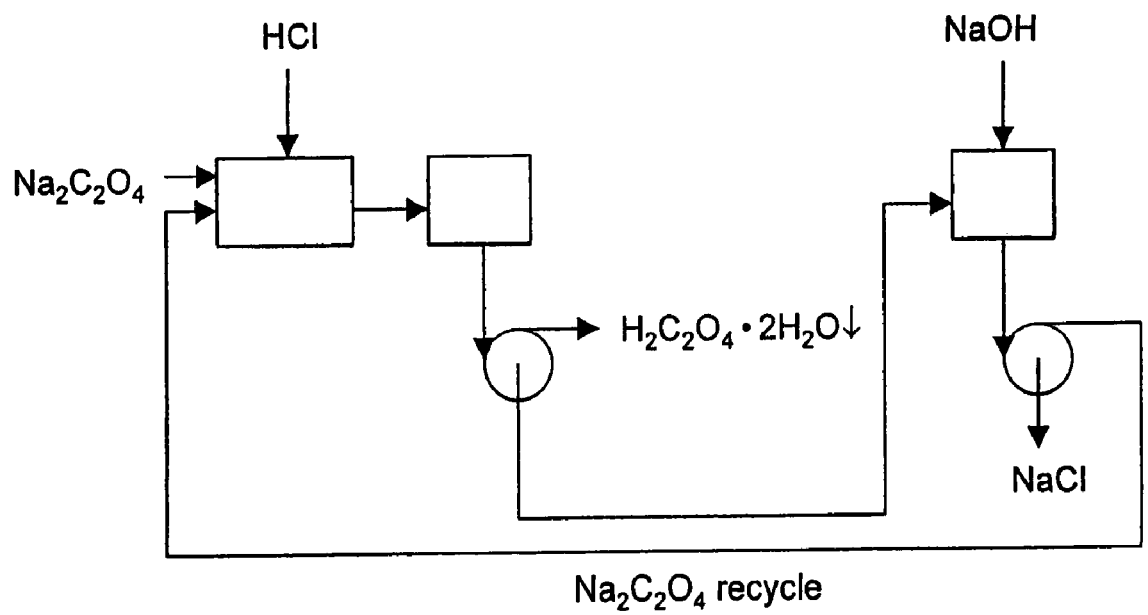
FIG. 2 shows a recycling variant of FIG. 1, in which the sodium oxalate reagent is transferred back to the beginning of the process.

After separation of the solid oxalic acid dihydrate, the residual solution contains unreacted hydrochloric acid and unprecipitated oxalic acid. As FIG. 2 shows, that residual solution may be treated by the addition of sodium hydroxide to neutralize these remaining acids, thereby forming sodium chloride in solution and regenerating sodium oxalate. The regenerated sodium oxalate may be precipitated, separated and returned to the front end or beginning of the process to be combined with the sodium oxalate feed.

Figure 3:
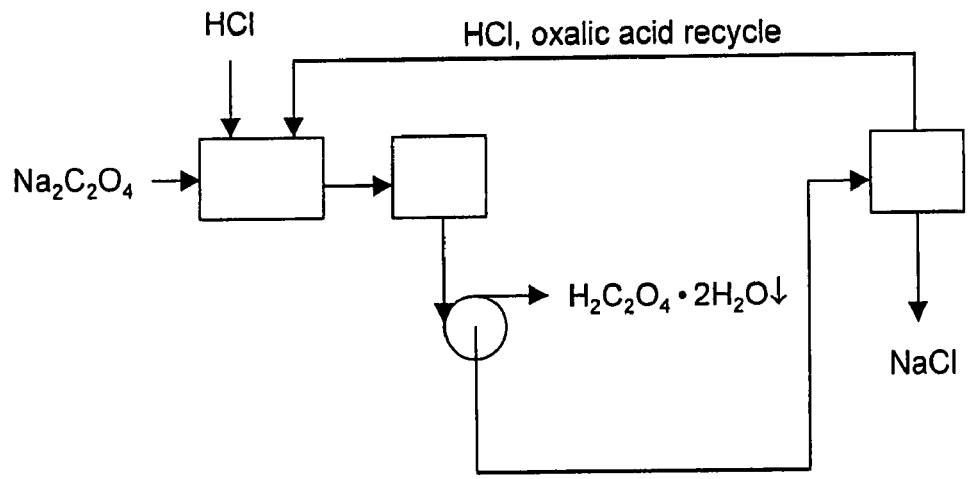
FIG. 3 shows a recycling variant of FIG. 1, in which hydrochloric acid and/or oxalic acid are recovered and recycled back to the reaction step.
Figure 4:
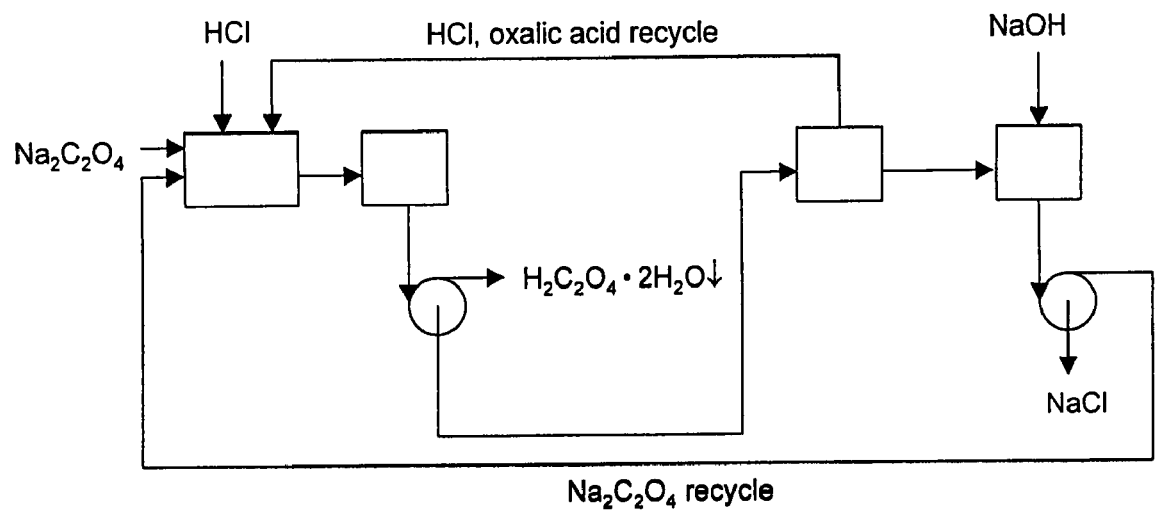
FIG. 4 shows a recycling variant of FIG. 3, in which the sodium oxalate reagent is transferred back to the beginning of the process

Before treating the residual solution that contains unreacted hydrochloric acid and unprecipitated oxalic acid with sodium hydroxide, the residual solution may optionally be processed for separation of the hydrochloric acid and oxalic acid by various techniques well known in the art such as distillation or extraction. FIG. 3 shows that the separated stream of hydrochloric acid and oxalic acid may be returned to the front end of the process to be combined with the hydrochloric acid feed. Finally, sodium oxalate can be regenerated, precipitated, separated and recycled after hydrochloric acid or oxalic acid or both hydrochloric acid and oxalic acid are first separated and recycled as shown in FIG. 4.

Any or all of the reaction steps in this process may be continuous. For example, the sodium oxalate and hydrochloric acid may continuously feed into the reaction chamber by separate feed streams or may be mixed into one feed stream, which then enters the reaction chamber. Moreover, the steps for recovery and recycling of the hydrochloric acid and/or the sodium oxalate after precipitation and removal of the oxalic acid may also be continuous. Recovery techniques from a residual solution, which functions as a waste stream, for both of these reactants are well known in the art, as is recycling of recovered products. Specifically, FIGS. 1 through 4 may depict a continuous manufacture, recovery and recycling process.

EXAMPLES

The following Examples further illustrate the process of manufacture of oxalic acid dihydrate described herein and allow one skilled in the art to ascertain its preferred features.

Example 1

Sufficient HCl 105.0 grams of deionized water was placed in a glass vessel. To the deionized water was added 100.0 grams of 37% hydrochloric acid and 33.5 grams of Aldrich sodium oxalate. The hydrochloric acid to sodium oxalate molar ratio was 4 to 1. The water to sodium oxalate molar ratio was 37.3. This mixture was heated on a hot plate at 80° C. while stirring for 60 minutes to form a colorless solution with the solids completely dissolved. After 60 minutes at 80° C., the glass vessel containing the solution was placed in an ice bath until the temperatures as measured by a thermometer in the solution and one just outside the glass vessel were both 2° C. White solids were observed to form in the solution.

These solids were filtered using a 0.45 micron 500 mL cellulose acetate filter funnel. The solids were washed with saturated aqueous solution of oxalic acid using 2 displacements (about 50 mL) and the total mass of colorless filtrate solution collected was 188.5 grams. The solids were dried overnight at 75° C. in a vacuum oven.

X-ray diffraction analysis (using an X'PERT Model 3040 automated powder diffractometer manufactured by PANalytical of Natick, Mass.) showed the solids to contain 17.8 grams of mixed oxalic acid dihydrate and anhydrous crystals of oxalic acid. The anhydrous crystals fraction is an artifact of the drying technique.

Figure 5:
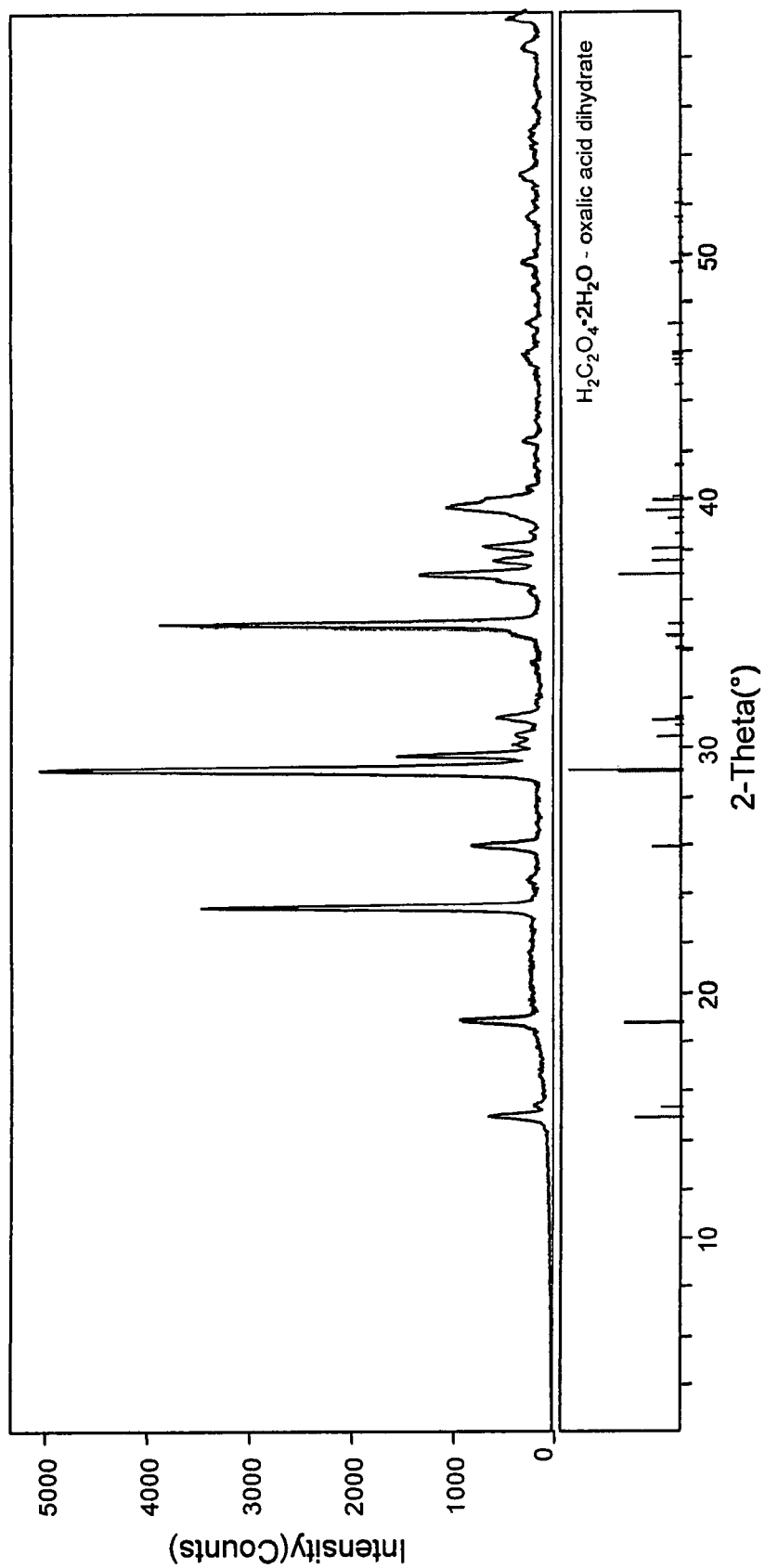
FIG. 5 shows an X-ray diffraction pattern of the separated solid of Example 1 indicating the presence of oxalic acid dihydrate.

FIG. 5 shows the X-ray diffraction pattern of the separated solid. This corresponds to a yield of at least 56% but not greater than 79% for the production of oxalic acid dihydrate.

Example 2

Insufficient HCl 130.0 grams of deionized water was placed in a glass vessel. To the deionized water was added 75.0 grams of 37% hydrochloric acid and 33.5 grams of Aldrich sodium oxalate. The hydrochloric acid to sodium oxalate molar ratio was 3 to 1. The water to sodium oxalate molar ratio was 39.4 to 1. This mixture was heated on a hot plate at 80° C. while stirring for 60 minutes to form a colorless solution with the solids completely dissolved. After 60 minutes at 80° C., the glass vessel containing the solution was placed in an ice bath until the temperatures as measured by a thermometer in the solution and one just outside the glass vessel were both 2° C. White solids were observed to form in the solution. These solids were filtered using a 0.45 micron 500 mL cellulose acetate filter funnel. The solids were washed with deionized water and the total mass of colorless filtrate solution collected was 224.7 grams. The solids were dried overnight under nitrogen at room temperature.

Figure 6:
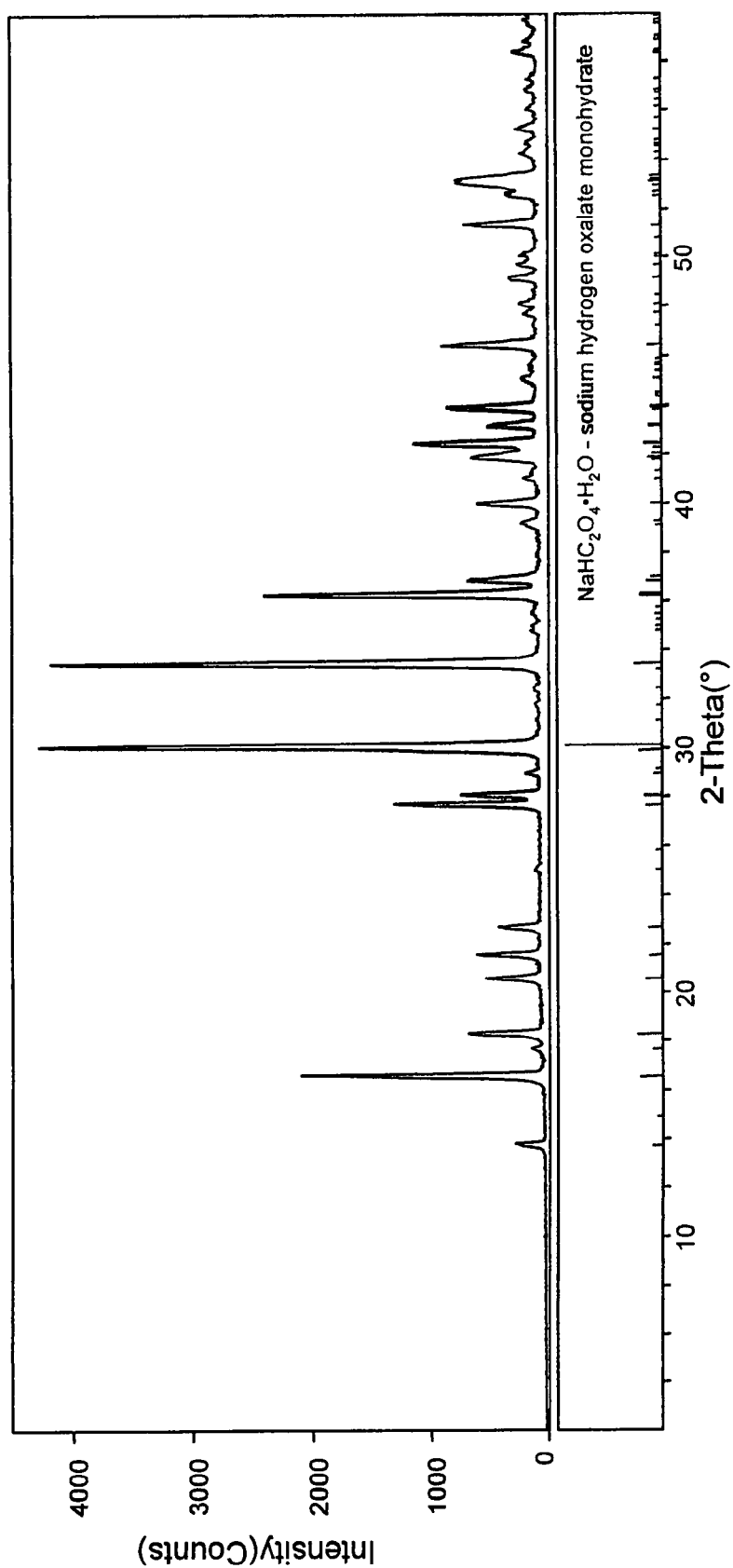
FIG. 6 shows an X-ray diffraction pattern of the separated solid of Example 2 indicating the presence of sodium hydrogen oxalate monohydrate.

X-ray diffraction analysis (using an X'PERT Model 3040 automated powder diffractometer manufactured by PANalytical of Natick, Mass.) showed the solids to contain 25.6 grams of sodium hydrogen oxalate monohydrate. FIG. 6 shows the X-ray diffraction pattern of the separated solid.

What is claimed is:

1. A process comprising:
   a) contacting an aqueous solution of hydrochloric acid with sodium oxalate in a reaction zone at a temperature between about 35° C. and about 140° C. to form a mixture wherein the solids are dissolved,
   wherein the molar ratio of the water to the sodium oxalate is between about 20 to 1 and about 350 to 1 and the molar ratio of the hydrochloric acid to the sodium oxalate is greater than about 3 to 1 and less than about 45 to 1;
   b) cooling the mixture to a temperature between about −10° C. and about 25° C. to form precipitated oxalic acid dihydrate in a slurry;
   c) separating the precipitated oxalic acid dihydrate from the slurry, thereby leaving a first residual solution;
   d) separating hydrochloric acid from the first residual solution, thereby leaving a second residual solution; and
   e) recycling the hydrochloric acid separated in step (d) to the reaction zone.

2. The process of claim 1, further comprising the steps of:
   f) separating oxalic acid from the first residual solution; and
   g) recycling both hydrochloric acid and oxalic acid separated in step (f) to the reaction zone.

3. The process of claim 1, further comprising the steps of:
   f) separating oxalic acid from the first residual solution, thereby leaving a third residual solution; and
   g) recycling the oxalic acids separated in step (f) to the reaction zone.

4. The process of claim 1, further comprising the steps of,
   f) neutralizing the second residual solution with a sodium-containing base to form precipitated sodium oxalate in a slurry;
   g) separating the precipitated sodium oxalate from the slurry; and
   h) recycling the separated sodium oxalate to the reaction zone.

5. The process of claim 1, wherein at least one step is done continuously.

6. The process of claim 2, wherein at least one step is done continuously.

7. The process of claim 3, wherein at least one step is done continuously.

8. The process of claim 4, wherein at least one step is done continuously.

9. The process of claim 1, wherein steps a and b are carried out in one reaction chamber.

10. A process comprising:
    a) contacting an aqueous solution of hydrochloric acid with sodium oxalate in a reaction zone at a temperature between about 35° C. and about 140° C. to form a mixture,
    wherein the molar ratio of the water to the sodium oxalate is between about 35 to 1 and about 350 to 1 and the molar ratio of the hydrochloric acid to the sodium oxalate is greater than about 2 to 1 and less than about 45 to 1;
    b) cooling the mixture to a temperature between about −10° C. and about 25° C. to form precipitated oxalic acid dihydrate in a slurry;
    c) separating the precipitated oxalic acid dihydrate from the slurry, thereby leaving a first residual solution;
    d) separating hydrochloric acid from the first residual solution thereby leaving a second residual solution; and
    e) recycling the hydrochloric acid separated in step (d) to the reaction zone.

11. The process of claim 10, further comprising the steps of:
    f) separating oxalic acid from the first residual solution; and
    g) recycling both hydrochloric acid and oxalic acid separated in step (f) to the reaction zone.

12. The process of claim 10, further comprising the steps of:
    f) separating oxalic acid from the first residual solution, thereby leaving a third residual solution; and
    g) recycling the oxalic acids separated in step (f) to the reaction zone.

13. The process of claim 10, further comprising the steps of,
    f) neutralizing the second residual solution with a sodium-containing base to form precipitated sodium oxalate in a slurry;
    g) separating the precipitated sodium oxalate from the slurry; and
    h) recycling the separated sodium oxalate to the reaction zone.

14. The process of claim 10, wherein at least one step is done continuously.

15. The process of claim 11, wherein at least one step is done continuously.

16. The process of claim 12, wherein at least one step is done continuously.

17. The process of claim 13, wherein at least one step is done continuously.

18. The process of claim 10, wherein steps a and b are carried out in one reaction chamber.

19. A process comprising:
    a) contacting an aqueous solution of hydrochloric acid with sodium oxalate in a reaction zone at a temperature between about 35° C. and about 140° C. to form a mixture,
    wherein the molar ratio of the hydrochloric acid to the sodium oxalate is greater than about 2 to 1 and less than about 45 to 1, and the concentration of hydrochloric acid in the aqueous solution of hydrochloric acid is no greater than about 18 wt %;
    b) cooling the mixture to a temperature between about −10° C. and about 25° C. to form precipitated oxalic acid dihydrate in a slurry;
    c) separating the precipitated oxalic acid dihydrate from the slurry, thereby leaving a first residual solution;
    d) separating hydrochloric acid from the first residual solution, thereby leaving a second residual solution; and
    e) recycling the hydrochloric acid separated in step (d) to the reaction zone.

20. The process of claim 19, further comprising the steps of:
    f) separating oxalic acid from the first residual solution; and
    g) recycling both hydrochloric acid and oxalic acid separated in step (f) to the reaction zone.

21. The process of claim 19, further comprising the steps of:
    f) separating oxalic acid from the first residual solution, thereby leaving a third residual solution; and
    g) recycling the oxalic acids separated in step (f) to the reaction zone.

22. The process of claim 19, further comprising the steps of,
    f) neutralizing the second residual solution with a sodium-containing base to form precipitated sodium oxalate in a slurry;

g) separating the precipitated sodium oxalate from the slurry; and h) recycling the separated sodium oxalate to the reaction zone.

23. The process of claim 19, wherein at least one step is done continuously.

24. The process of claim 20, wherein at least one step is done continuously.

25. The process of claim 21, wherein at least one step is done continuously.

26. The process of claim 22, wherein at least one step is done continuously.

27. The process of claim 19, wherein steps a and b are carried out in one reaction chamber.

* * * * *